United States Patent [19]

Azema et al.

[11] Patent Number: 4,973,330
[45] Date of Patent: Nov. 27, 1990

[54] SURGICAL APPARATUS FOR MODIFYING THE CURVATURE OF THE EYE CORNEA

[75] Inventors: Alain Azema; Jacques Arneodo; Jean Botineau; Philippe Crozafon; Gérard Moulin, all of Nice, France

[73] Assignee: Synthelabo, Paris, France

[21] Appl. No.: 918,825

[22] PCT Filed: Jan. 30, 1986

[86] PCT No.: PCT/FR86/00026
§ 371 Date: Sep. 25, 1986
§ 102(e) Date: Sep. 25, 1986

[87] PCT Pub. No.: WO86/04500
PCT Pub. Date: Aug. 4, 1986

[30] Foreign Application Priority Data

Feb. 4, 1985 [FR] France .................. 85 01614

[51] Int. Cl.$^5$ .............................. A61N 5/06
[52] U.S. Cl. ...................... 606/005; 606/10; 606/17; 128/395; 219/121.75; 219/121.83
[58] Field of Search ............ 128/303.1, 395, 396; 219/121 L, 121 LB, 121 LE, 121 LG, 121 LH, 121 LP, 121 LR, 121 LZ; 606/5, 10, 13, 17

[56] References Cited

U.S. PATENT DOCUMENTS

| 3,096,767 | 7/1963  | Gresser .           |          |
|-----------|---------|---------------------|----------|
| 3,703,176 | 11/1972 | Vassiliadis et al.  | 128/303.1|
| 3,720,213 | 3/1973  | Hobart et al.       | 128/303.1|
| 3,769,963 | 11/1973 | Goldman .           |          |
| 3,796,220 | 3/1974  | Bredemeier          | 128/303.1|
| 3,821,510 | 6/1974  | Muncheryan          | 128/303.1|
| 4,165,744 | 8/1979  | Cravy et al.        | 128/303.1|
| 4,461,294 | 7/1984  | Baron .             |          |
| 4,648,400 | 3/1987  | Schneider           | 128/303.1|
| 4,665,913 | 5/1987  | L'Esperance, Jr.    | 128/303.1|
| 4,729,372 | 3/1988  | L'Esperance, Jr.    | 128/303.1|

FOREIGN PATENT DOCUMENTS 215698 11/1984 Fed. Rep. of Germany ... 128/303.1

OTHER PUBLICATIONS

Trokel et al., American Journal of Opthalmogy, vol. 96, No. 6 (Dec. 6, 1983), pp. 710-715.
European Published Pat. Appln. 0111060.
Taboada et al., Health Physics, vol. 40, (May 1981), pp. 677-683.
European Published Pat. Appln. No. 0151869.

Primary Examiner—Lee S. Cohen
Assistant Examiner—David Shay
Attorney, Agent, or Firm—Fisher, Christen & Sabol

[57] ABSTRACT

A surgical apparatus for partially modifying the curvature of the cornea of an eye while the eye is within the patient is disclosed. The device is able to ablate a zone of corneal material in the form of a lenticular lamina. The thickness of the lamina at any particular point on the cornea surface varies as a function of the radial distance between that point and the central optical axis of the eye. The surgical apparatus comprises: a source of light (31) capable of emitting a beam of light (4) having a wavelength which is about 200 nanometers; an optical system (32) for directing and focusing the beam of light onto the desired zone of the cornea in order to ablate a lamina of material of the desired dimensions; and, a series of diaphragms and screens for obscuring varying portions of the zone of the cornea undergoing ablation in order to effect differential irradiation of the corneal surface. The longer the light beam (4) is allowed to impinge a particular portion of the cornea, the more corneal material removed from that spot and the greater the thickness of the lamina (2 and 16), and vice versa.

33 Claims, 5 Drawing Sheets

SURGICAL APPARATUS FOR MODIFYING THE CURVATURE OF THE EYE CORNEA

The present invention relates to a surgical apparatus for modifying the curvature of the eye cornea. The apparatus may be utilized both with corneas which are in situ within a living being as well as with corneas which have previously been removed from the patient's body.

It is known that certain disorders, such as myopia, hypermetropia and astigmatism, may be treated by modifying the curvature of the cornea. Furthermore, other disorders, such as aphakia, may be treated at least partly by correction of said curvature. Consequently, methods for modifying the curvature of the cornea have already been thought of.

Such methods are essentially of two types:

The first consists of the steps of: (1) removing with the aid of a mechanical cutting instrument, a plane-convex lens-shaped body of material from the cornea, (2) freezing this lens to render it solid and (3) machining, by means of a lathe, said solidified lens in order to eliminate therefrom a zone in the form of a convex lamina of variable thickness. After machining, the machined lens is thawed, then sewn back at its initial location. Such a method is long, expensive and traumatic for the patient. Moreover, this method can only be used to treat disorders wherein the extent to which the radius of curvature of the cornea is suboptimized is constant about the optical axis of the eye, such as myopia and hypermetropia, but is of no usefulness with disorders such as astigmatism wherein the amount of corneal material which must be removed in order to optimize the shape of the cornea does not present any symmetry of revolution about the optical axis;

in the second type of method, a series of radial slots are made in the cornea, outside of the optical zone, by means of a bistoury or a laser beam. As a result of these slots, the incized part of cornea flattens, consequently modifying the general curvature. Although less traumatic than the methods of the first type, those of the second type remain violent due to necessary scarifications of the cornea. Moreover, the possible applications for these latter methods remain limited.

In contrast to the above-stated methods, the article entitled "Excimer laser surgery of the cornea" dated Sept. 21, 1983 and appearing in the Journal "AMERICAN JOURNAL OF OPHTHALMOLOGY", Vol. 96, No. 6, pages 710 to 715 of December 1983, by STEPHEN L. TROKEL, R. SRINIVASAN and BODIL BRAREN discloses the use of an excimer laser to modify the corneal profile by photodecomposition. In this article, the use of a source of ultraviolet radiation having a wavelength equal to 0.193 micrometer (193 nanometers) in order to modify the curvature of the cornea is disclosed. This method calls for forming on said cornea, with the aid of said radiation, a circular photoradiant zone "of which the intensity varies from the center towards the periphery, with the result that more matter is removed either at the center or on the periphery, as a function of the distribution of light". The curvature of the cornea may thus be increased or reduced.

This latter method is particularly advantageous, but is difficult to carry out, as it calls for varying the light intensity within the photoradiant zone in accordance with the desired corneal curvature. Putting this method into practice appears difficult if not impossible.

It is an object of the present invention to overcome the drawbacks of these known methods. The present invention relates to a surgical apparatus for modifying the curvature of the cornea in a non-traumatic, rapid and easy manner in order to treat disorders as different as myopia, hypermetropia, aphakia, and astigmatism.

Towards these ends, a surgical apparatus for modifying at least partly the curvature of the eye cornea by ablation of a zone therefrom having the form of a lenticular lamina of radially variable thickness is disclosed. The apparatus comprises a source of light capable of emitting a beam whose wavelength is close to 0.2 micrometer (i.e., about 200 nm) in order to produce the desired photodecomposition of the corneal matter, as well as an optical system for directing said beam onto the cornea zone which is to be eliminated and thereby forming a spot of light on a part of said zone. This apparatus is noteworthy in that it comprises means for irradiating, with said light spot, the whole of said zone to be eliminated for varying lengths of time, with the result that the longer a particular portion of said zone is exposed to said beam, the thicker the lenticular lamina of corneal material which is removed, and vice versa.

In this way, ablation of the corneal matter may be obtained without scarification by a photochemical process, particularly non-traumatic for the patient, without having to design means capable of varying the intensity of the laser beam radially.

Therefore, a light source of substantially constant intensity may be utilized. According to the present invention, those areas of the cornea which require the removal of larger thicknesses of material are exposed to the light source for longer periods of time, and those areas requiring the removal of only small thicknesses of corneal material are exposed to the light source for shorter periods. In this way, a differential photochemical ablation of the cornea is obtained, making it possible to modify the curvature thereof, since these thick parts receive more light energy than these thin parts.

The progressivity of this differential photochemical ablation then depends solely on the progressivity of the selective obscurification, or scanning of the whole of the zone to be eliminated by said light spot.

In order to obtain the maximum precision in the modification of the curvature of the cornea, two modes of scanning are provided according to the invention:

1—According to the first mode, the light spot remains constantly centered on the optical axis of the eye at all times. Under this mode of operation, the invention comprises scanning means for progressively varying the area of this spot on the cornea. This mode is applicable virtually to all treatments. In fact:

(a) The treatment of myopia—correctable by a reduction of the curvature of the cornea—necessitates the ablation of a lamina in the form of a lens, thicker at its center (vicinity of the optical axis of the eye) than on its periphery. Consequently, in this case, the density of light energy received by the cornea must decrease from the center towards the periphery, or stated differently, increase from the periphery towards the center.

Towards this end, the optical system of the apparatus according to the invention forms on the cornea a circular light spot and said scanning means progressively varies the area of said spot from a mall central spot to the total area of the zone to be eliminated, or vice versa. If in a particular case, it is desirable to gradually increase the size of the spot, i.e., from the center towards the periphery, the duration of exposure to the light beam decreases as one moves away from the center. On the other hand, when scanning of the zone of corneal material to be eliminated takes place from the periphery towards the center, the duration of exposure to the light beam increases as one moves towards the center. Of course, in either case, the variation of the duration of exposure is adjusted in order to produce the desired variation of curvature.

(b) The treatment of hypermetropia and aphakia—correctable by increasing the curvature of the cornea—necessitates the ablation of a lamina which is thicker on its periphery than at its center (vicinity of the optical axis). Consequently, in that case, the total density of light energy received by the cornea must increase from the center towards the periphery or decrease from the periphery towards the center.

Towards this end, the optical system of the apparatus according to the invention is capable of forming a darkened spot on the cornea wherein said photoradiant energy is blocked. The scanning means progressively varies the area of said spot, at least by varying the diameter thereof. Of course, such variation in the area of the obscured spot is adjusted so that the desired modification of the corneal profile is obtained. This variation may be effected both by starting with a maximally-sized spot and gradually decreasing its size, or by starting with a minimally-sized spot and gradually increasing its size.

(c) The treatment of astigmatism (due to the corneal surface exhibiting different radii of curvature along its different meridians necessitates a correction of curvature along a particular meridian plane passing through the optical axis. Thus, in this case, the zone of photoradiant energy formed on the surface of the cornea is not centered on the optical axis, but rather forms on the cornea an elongated light spot which can be viewed as approximately rectangular in shape. The two longer sides of the spot are perpendicular to said particular meridian. The scanning means of the present invention progressively varies the area of said spot, a least by varying the length of the two smaller sides thereof.

In this case as well, the variation in area of the irradiated zone may be produced by either enlarging or reducing the size of the spot. The important constraint is that the variation is such (as a function of time) that it communicates to the cornea the desired modification of curvature.

2—According to a second mode for utilizing the present invention to modify the curvature of the cornea surface, the zone of photoradiation impinged upon the corneal surface is in the shape of a simple geometrical form defined by segments of straight lines, for example, a rectangle. Under this mode of operation, the apparatus of the present invention causes the light spot to occupy a plurality of successive positions, the duration of hold of the spot in any one of these positions depending upon the desired thickness of the corneal matter to be eliminated at that location.

In this situation, it is seen that the whole zone of cornea material to be eliminated may easily be covered by sequential juxtaposition of said spot, due to the particular simple geometrical form utilized for the zone of photoradiant energy in this situation.

This second mode of modifying curvature according to the invention is therefore particularly appropriate for the correction of astigmatism, and serves a variant to the first mode described hereinabove which may also be utilized towards that end. It is thus advantageous, in order to facilitate the process of juxtaposition, if said spot covers the whole of the width of the zone to be eliminated and if said scanning means is capable of displacing said spot parallel to itself in a direction perpendicular to this width across the area of the cornea material to be eliminated.

Whatever the mode of correction of curvatures within which the apparatus according to the invention functions, it is crucial that the scanning means be utilized in order to produce a total discharge of photoradiant energy as a function of time suitable for leading to the desired modified curvature.

In a preferred embodiment of the surgical apparatus according to the invention, said scanning means comprise at least one screen or diaphragm and displacement means for creating a relative displacement between said optical system and at least one of said screens or diaphragms, the speed of this relative displacement corresponding to the radial variation in thickness of said lamina to be eliminated. Depending on the case, the direction of this relative displacement may be parallel or transverse to said beam.

Said optical system and said screens and/or diaphragms are advantageously mounted on an optical bench.

Thus, to treat myopia, the apparatus according to the invention comprises:
  either a fixed diaphragm and a mobile optical system, receiving the beam issuing from said diaphragm;
  or a first fixed diaphragm, a likewise fixed optical system receiving the beam issuing from said first diaphragm and a second mobile diaphragm disposed on the side opposite the first diaphragm with respect to said optical system.

Similarly, to treat hypermetropia and aphakia, the apparatus according to the invention comprises:
  either a fixed diaphragm, a mobile optical system receiving the beam issuing from said diaphragm and a screen, which is fast in displacement with said optical system and which occults the central part of the beam passing therethrough;
  or a fixed diaphragm, a likewise fixed optical system receiving the beam issuing from said diaphragm and a mobile screen, which occults the central part of the beam passing through said optical system.

To treat astigmatism, the apparatus according to the invention may comprise a fixed diaphragm, a likewise fixed optical system and a mobile screen pierced with a slot. This slot is transverse to the direction of displacement of said screen and may be displaced either parallel to itself or in its own plane. The apparatus in that case advantageously comprises means for adjusting the orientation of said slot in the plane of said mobile screen.

In order to obtain an automatic surgical apparatus, it is advantageous to provide an electronic computer for controlling said source of light and said scanning means as a function of the desired radial variation in thickness for said lamina of corneal material to be eliminated. The apparatus in that case further comprises a keratometer capable of following the modification of curvature of the cornea and of addressing its measurements to said computer. In order to facilitate alignment of the ablation beam with respect to said cornea, an auxiliary laser generator is also provided, for example of the helium-neon type.

The Figures of the accompanying drawing will clearly show how the invention may be carried out. In these Figures, identical references designate similar or like elements.

Figure 1:
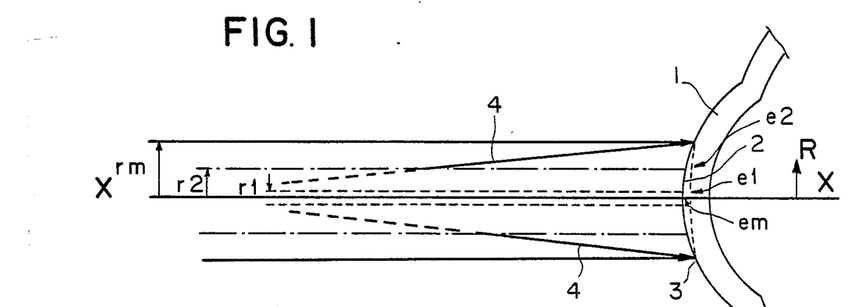
FIG. 1 schematically illustrates, in axial view, the principle according to which the apparatus of the invention functions in the case of treatment of myopia.
Figure 2:
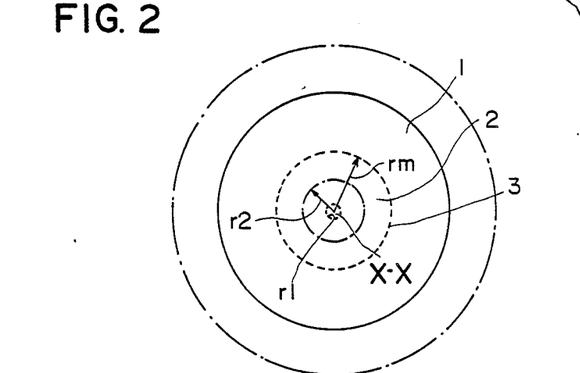
FIG. 2 schematically illustrates, in front view, the principle according to which the apparatus of the invention functions in the case of the treatment of myopia.

FIGS. 1 and 2 illustrate the principle according to which the apparatus of the present invention functions, in the case of treatment of myopia.

These Figures schematically show, in axial section and in front view respectively, the cornea 1 of a myopic eye.

In known manner, such a myopic defect is known to be surgically correctable by eliminating a lamina 2 having the form of a circular lens, so as to reduce the overall curvature of the cornea.

This lenticular lamina 2 is centered on the optical axis X—X of the eye and presents at its center a maximum thickness em, which decreases towards its periphery 3, as a function of the radial distance R to the axis X—X.

The progressivity of the variation in thickness e of said lamina 2 as a function of the variation in the radial distance R determines the extent of the desired correction of curvature.

According to the invention, in order to obtain ablation of lamina 2 having a variation of thickness as a function of the radial distance away from the optical axis X—X which can be characterized by the expression e (R), a light beam 4 of circular section is used. The light beam 4 has a wavelength which is at the most equal to 0.2 micrometer (200 nm) and which presents a substantially constant energy density across the cross-section of the beam 4. The light beam 4 is directed onto the cornea 1 and centered on the optical axis X—X.

As is best seen in FIG. 2, through the use of means which will be described hereinafter with reference to FIGS. 3 and 4, the radius r of the spot formed by said beam 4 on the cornea 1 is varied, as a function of time t, in such a way that it is possible to produce the desired function of ablation: e (R), i.e., such that, for each value $0,...,r1,...,r2,...,rm$ of the radius of said spot, a depth of elimination of cornea is obtained, corresponding to the thicknesses $em,...,e1...e2,...0$ of said lamina 2. As can be seen, in the case of correction of myopia, the thickness, e, of said lamina is inversely related to the length of the radius r away from the optical axis X—X at any particular point.

Of course, the variation r (t) of radius r as a function of time t may be made from maximum value rm of the radius r towards zero, or from zero towards the maximum value rm. That is, the beam 4 may be focused to form a very small spot around the optical axis X—X and then adjusted to form a gradually larger spot, or the process may be initiated with a spot of maximum, rm, radius which is gradually decreased.

It is thus seen that, according to the invention, the desired ablation of lamina 2 is obtained by forming, on cornea 1, a circular light spot and by varying the radius of this spot as a function of time, in order to obtain ablation of the desired volume of corneal material.

Figure 3:
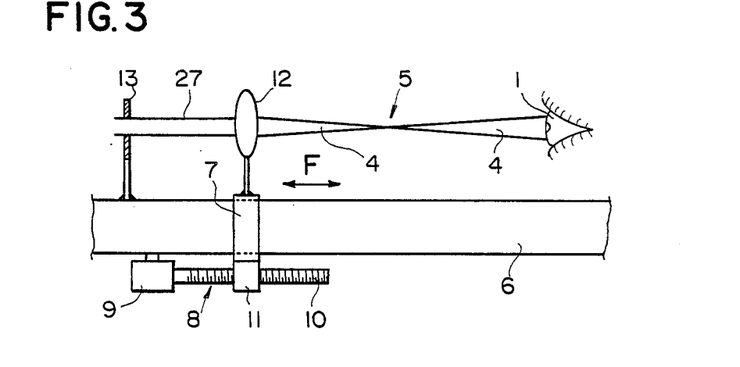
FIG. 3 shows a diagram of one embodiment of part of the apparatus according to the invention, when it is intended for the treatment of myopia.
Figure 4:
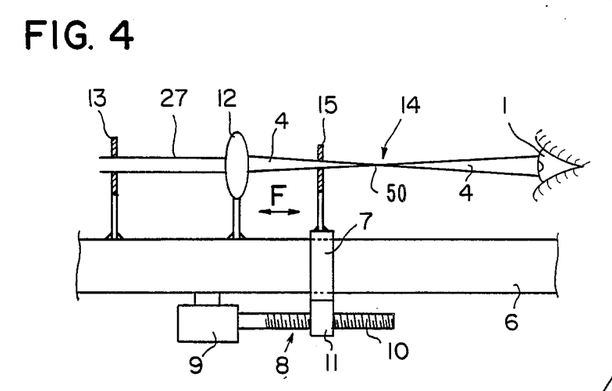
FIG. 4 shows a diagram of another embodiment of part of the apparatus according to the invention, when it is intended for the treatment of myopia.

In order to obtain this light spot of variable diameter, appropriate for the treatment of myopia, one or the other of the devices shown schematically in FIGS. 3 and 4 may be used.

The device 5 shown in FIG. 3 comprises an optical bench 6 along which a carriage 7 may move in both directions (arrows F), under the action of drive means 8 which may include for example an electric motor 9 driving an endless screw 10, cooperating with a nut 11 connected to said carriage 7, in rotation.

Carriage 7 bears an optical system shown in the form of a lens 12 focusing the light beam 4 and capable of forming a light spot on the cornea 1. By varying the position of the lens 12, thanks to carriage 7, the radius of said spot on said cornea can be varied. For example, by moving the lens 12 away from the light source (not shown, but implied to be on the left in FIG. 3, the light source is also shown schematically as 31 on FIG. 13 discussed hereinafter) a spot having a smaller radius r will be produced on the cornea. Conversely, by moving the lens 12 closer to the light source, a spot having a larger radius will be produced on the cornea 1. By monitoring the speed of displacement of carriage 7 along the bench 6, for example, through the use of drive means 8, it is possible to produce the desired variation of the radius r, of the spot as a function of time (i.e., r (t)) and thereby produce the desired variation in the volume of ablated material as a function of the radius r away from the optical axis X—X (i.e., e (R)).

A fixed diaphragm 13 makes it possible to address to lens 12 an essentially homogeneous, parallel light beam 27 of circular section, which is focused to form light beam 4. That is, only that light 27 produced by the light source which is relatively unidirectional will not be blocked by fixed diaphragm 13.

In the variant embodiment 14 shown in FIG. 4, the lens 12 is permanently mounted on bench 6. In this embodiment, an additional circular diaphragm 15 is provided, mounted on carriage 7. Through the use of the drive means 8, the diaphragm 15 is displaced along bench 6 and, consequently, the dimensions of the spot formed by beam 4 on cornea are varied. For example, when the diaphragm 15 is positioned fairly near to the focal point 50 of the light beam 4, the entire light beam 4 is allowed to pass through the diaphragm 15 unobstructed and thus a light spot having the maximum radius, rm, is produced on the cornea 1. On the other hand, as the carriage 7, is moved to the left, towards the light source, the diaphragm will increasingly obscure the outer portions of the light beam 4, and thus a spot of decreasing radius will be produced.

Figure 5:
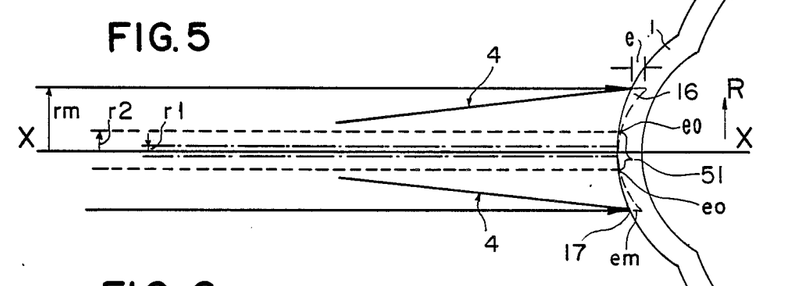
FIG. 5 schematically illustrates, in axial view the principle according to which the apparatus of the invention functions, in the case of treatment of hypermetropia and of aphakia.
Figure 6:
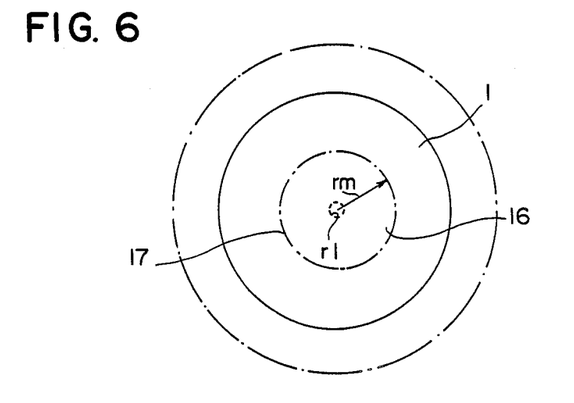
FIG. 6 schematically illustrates, in front view, the principle according to which the apparatus of the invention functions, in the case of hypermetropia and of aphakia.

Referring now to FIGS. 5 and 6, the principle according to which the apparatus of the present invention functions for the treatment of hypermetropia and aphakia is explained. In this case, it is known that such defects may be corrected surgically by eliminating a lamina 16 in the form of a meniscus which is thinner at the center than at its edges, so as locally to increase the curvature of the cornea.

The lamina 16 is again centered on the optical axis X—X of the eye and presents a thickness e which increases towards its periphery 17. Therefore, in the treatment of hypermetropia and aphakia, the lamina 16 of corneal material which must be removed in order to optimize the radius of curvature of the corneal surface has a maximum thickness em, at the periphery 17, and a minimum thickness eo at, or near, the optical axis X—X (i.e., where r=o).

By analogy with what has been described with reference to FIGS. 1 and 2, it will be readily understood that, with the aid of the light beam 4 and means for forming an annular spot of darkened area 51 on the cornea 1, as will be more fully discussed hereinafter with reference to FIGS. 7 and 8, ablation of the lamina 16 may be effected by varying the inner radius of said spot 51 as a function of time, in order to ablate a lamina 16 of appropriate dimensions.

In this case, contrary to what was mentioned for the treatment of myopia, the duration of exposure to the beam 4 will increase as one moves away from the optical axis X—X, i.e., as the length of the radius, r, increases.

Figure 7:
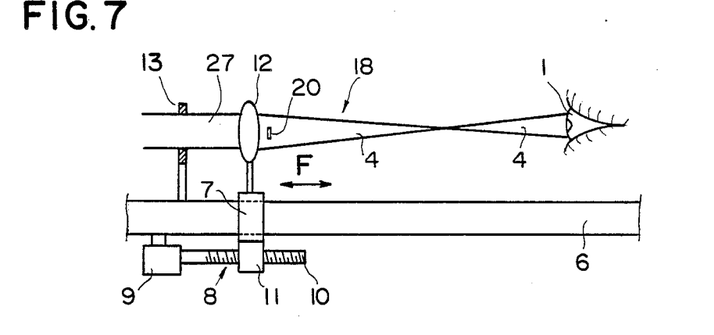
FIG. 7 shows a diagram of one embodiment of part of the apparatus according to the invention, when it is intended for the treatment of hypermetropia and aphakia.
Figure 8:
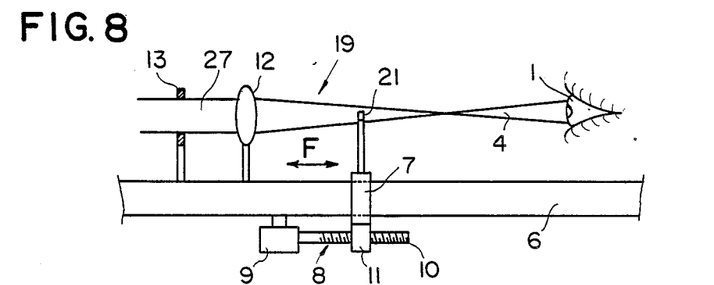
FIG. 8 shows a diagram of another embodiment of part of the apparatus according to the invention, when it is intended for the treatment of hypermetropia and aphakia.

To carry out the process illustrated in FIGS. 5 and 6, one or the other of the devices 18 and 19 of FIGS. 7 or 8 may be used.

Device 18 is identical to device 5 of FIG. 8, except that the central part of the lens 12 is blocked by a circular central screen 20. Consequently, when the drive means 8 displace the lens 12 along the bench 6, a variation in the dimensions of the shadow made by said screen 20 on the central part of said cornea 1 results. For example, as the lens 12 is moved closer to the screen 20, only a small portion, e.g., 51, at the center of the cornea 1 will be darkened, whereas when the lens is moved away from the screen 20, a progressively larger portion of the beam 4 will be blocked, and hence progressively more of the corneal surface 1 will be darkened. By adjusting the speed of displacement of the assembly 12, 20 along bench 6 (thanks to the control of drive means 8), the time of exposure of the various portions of the cornea 1 to the beam 4 is adjusted as a function of the radial distance away from the optical axis X—X, in order to obtain ablation of the lamina 16 of desired profile.

An identical result is obtained by using device 19 which is similar to device 14 of FIG. 4, except that instead of a diaphragm 15 which blocks the outer portions of the light beam 4, this version of the device employs a circular screen 21 mounted on the carriage 7 for blocking the central portion of the light beam 4. The displacement of carriage 7 along the bench 6 and the resultant movement of the screen produced thereby results in the creation of an area of shadow 51 on the central part of the cornea 1.

Figure 9:
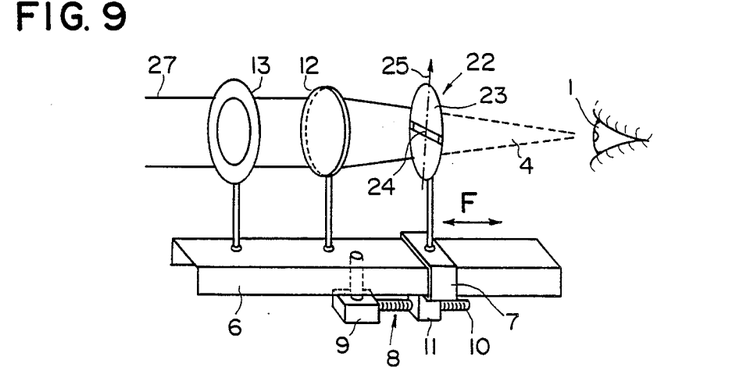
FIG. 9 schematically shows an embodiment of part of the apparatus according to the invention, when it is intended for treatment of astigmatism.

FIG. 9 partially and schematically shows in perspective a device 22 according to the invention, intended for correcting astigmatism. This device 22 is identical to device 14 of FIG. 4, except that the circular diaphragm 15 is replaced by a screen 23, pierced with a rectilinear slot 24. The rectilinear slot 24 is orthogonal to a predetermined direction 25.

Figures 10, 11, 12:
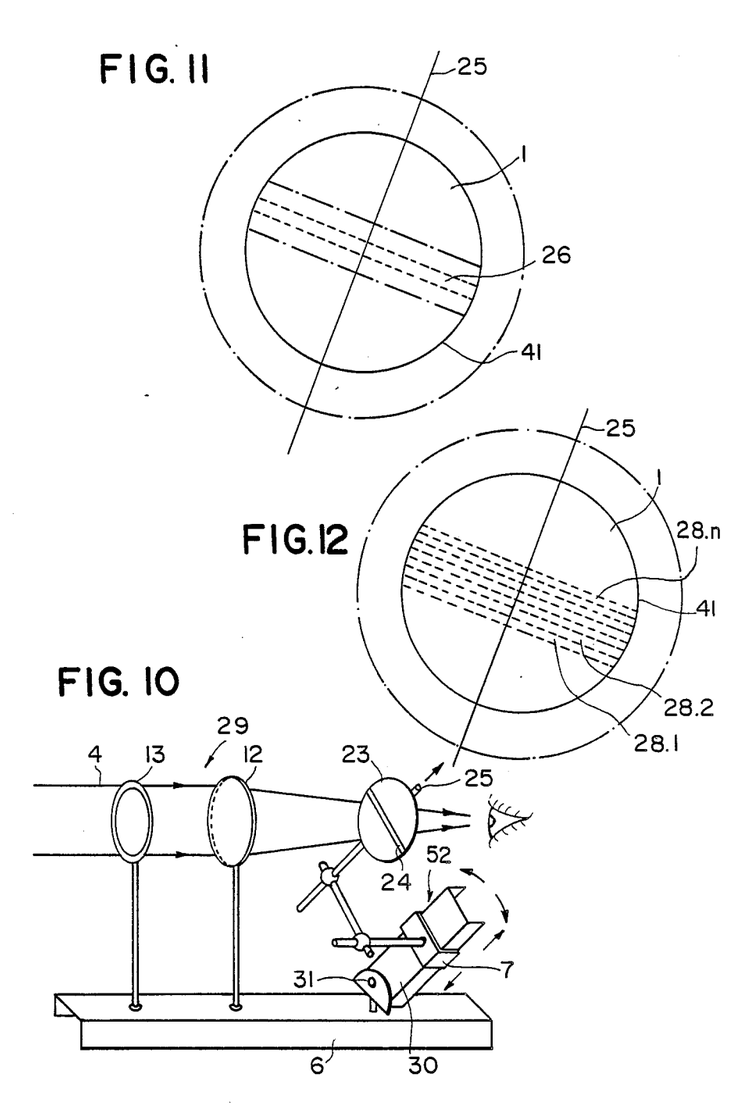
FIG. 10 schematically shows another variant embodiment of part of the apparatus according to the invention, when it is intended for treating astigmatism.
FIG. 11 schematically illustrates the functioning of the embodiment of FIG. 9.
FIG. 12 schematically illustrates the functioning of the embodiment of FIG. 10.

Thus, as illustrated in FIG. 11, by means of this version of the device 22, there is formed on the cornea 1 an elongated light spot 26 which is essentially rectangular in shape. The two longer sides of this spot 26 are orthogonal to said predetermined direction 25, which corresponds to the outline of the meridian of the eye along which the correction of curvature is to be effected. Laterally, the length of the two longer sides of said spot 26 is limited by the circular line 41 which is determined by the dimensions of the diaphragm 13.

During displacement of carriage 7 and screen 23 (under the action of means 8 to 11) along bench 6, the area of the spot 26 on the cornea increases and/or decreases as a function of the direction of said displacement, with the result that it is possible to produce the ablation of a lamina corresponding to the desired correction.

Devices 5, 14, 18, 19 and 22 shown and described with reference to FIGS. 3, 4, 7, 8 and 9 scan the cornea 1 by varying the area of a light spot and/or darkened area 51 on the surface of the cornea. However, ablation of corneal material may also be effected by moving a light spot whose dimension parallel to scanning remains constant across the surface of the cornea 1.

For example, FIG. 10 illustrates a variant 29 of the device according to the invention. In this embodiment, the screen 23 is mounted on a controllable device 52 so that it may be displaced in its plane perpendicular to the light beam 4. In this case, scanning of the zone of cornea 1 to be eliminated is effected by moving the light spot 28 formed on the cornea 1 by the slot 24 in the screen 23 through a plurality of successive positions 28.1,...,28.n as shown in FIG. 12. The duration of time during which the light spot 28 is held in each of its positions 28.1 to 28.n, depends on the thickness of corneal matter to be eliminated at the particular location in question.

It is noted that, in the device 29 of FIG. 10, the screen 23 may be moved not only in its plane, but, thanks to an articulation device 31 of its support 30, may be oriented so that the direction of slot 24 is adjustable.

Figure 13:
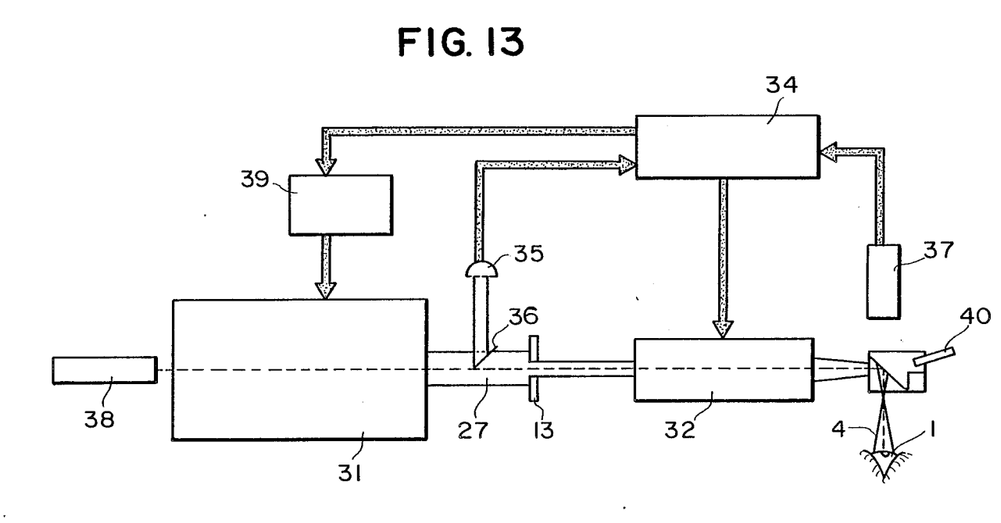
FIG. 13 is the overall block diagram of the apparatus according to the invention.

FIG. 13 shows a block diagram of an automatic version of the apparatus according to the present invention.

As shown schematically in FIG. 13, the apparatus comprises:

a light source 31 capable of emitting a light beam 27 of essentially uniform energy intensity whose wavelength is at the most equal to 0.2 micrometer (i.e., 200 nm), for example an excimer laser generator, of the argon-fluorine mixture type;

a system 32 directing said light beam, after passage through diaphragm 13, said diaphragm 13 blocking the passage of all light which is not essentially unidirectional in nature, towards the cornea 1 and comprising means for impinging said light beam 4 on various areas of the cornea 1; the system 32 employed may be one or the other of devices 5, 14, 18, 19, 22, 29 described hereinabove, or a similar device;

an electronic computer 34 charged with controlling the process and functioning of said apparatus and in particular with controlling the device 32 (and especially the drive means 8);

a photodetector 35, associated with a semi-transparent mirror 36 and intended to furnish the computer 34 with the information relative to the energy of the pulses of beam 4;

an automatic keratometer 37 which measures in real time the curvature of the cornea 1 and transmits its measurements to computer 34;

an alignment laser 38, for example of the helium-neon type, allowing a correct positioning of the beam 4 on the cornea 1;

a device 39 for controlling the source of light 31, itself controlled by computer 34; and a slotted lamp 40 enabling the surgeon to observe the cornea 1 during operation.

Computer 34 is programmed to control device 32 so as to produce ablation of a lamina of corneal material having the desired thickness in order to produce a corneal surface having an optimized curvature. The computer 34 carries out the corresponding sequences of operations by taking into account the information furnished thereto by the keratometer 37 and the photodetector 35.

We claim:

1. Surgical apparatus for modifying at least partly the curvature of the cornea of an eye having a central optical axis by ablation of a zone thereof which has the form of a lenticular lamina, the thickness of said lamina at any particular point varies as a function of the radial distance to the central optical axis of the eye with the result that the desired modification of curvature of the cornea is produced, comprising:
   (a) a source of light capable of emitting light having a wavelength which is close to 200 nanometers;
   (b) means for selecting out of the light emitted by said light source a portion of light which is essentially unidirectional in nature, whereby a beam of light having a width is formed, said beam having a substantially constant energy density transversely across the width of said beam, whereby said beam is able to produce photodecomposition of corneal matter;
   (c) an optical system for directing said beam onto the zone of the cornea to be eliminated and for forming thereon a light spot constantly centered on said optical axis; and,
   (d) means for progressively varying the surface area of said light spot on the cornea, so that the length of time said beam is allowed to impinge on a particular portion of said zone of the cornea and the thickness of the corneal material which is to be eliminated at a particular location are directly related, whereby the areas of the cornea which constitute the thicker portions of said lamina are exposed to said beam for longer periods of time and the areas of the cornea which constitute the thinner portions of said lamina are exposed to said beam for shorter periods of time.

2. Apparatus according to claim 1, characterized in that said light spot is circular.

3. Apparatus according to claim 1, characterized in that said light spot is annular.

4. Apparatus according to claim 1, characterized in that said light spot is substantially rectangular.

5. Apparatus according to claim 1, characterized in that said apparatus comprises scanning means for causing said spot to occupy a plurality of different successive positions.

6. Apparatus according to claim 5, characterized in that successive positions of the light spot cover a juxtaposition of the zone to be eliminated.

7. Apparatus according to claim 5, characterized in that said spot covers a whole width of the zone to be eliminated and in that said scanning means displace this spot parallel to itself, in a direction perpendicular to this width.

8. Apparatus according to claim 1 characterized in that scanning means comprise at least one screen or diaphragm and displacement means for creating a relative displacement between said optical system and at least one of said screens or diaphragms, this relative displacement occurring at a speed corresponding to the variation in thickness of said lamina to be eliminated.

9. Apparatus according to claim 8, characterized in that said displacement means create a relative displacement of direction parallel to said beam.

10. Apparatus according to claim 8, characterized in that said displacement means create a relative displacement of direction transverse to said beam.

11. Apparatus according to claim 9, characterized in that said optical system and said screens are mounted on an optical bench.

12. Apparatus according to claim 9, characterized in that said apparatus comprises a fixed diaphragm and a mobile optical system receiving a parallel beam issuing from said diaphragm.

13. Apparatus according to claim 9, characterized in that said apparatus comprises a first fixed diaphragm, a fixed optical system receiving a parallel beam issuing from said first diaphragm and a second mobile diaphragm, disposed on a side opposite the first diaphragm with respect to said optical system.

14. Apparatus according to claim 9, characterized in that said apparatus comprises a fixed diaphragm, a mobile optical system receiving a parallel beaming issuing from said diaphragm and a screen, which is held immobile with respect to said optical system and which occults a central part of the beam passing therethrough.

15. Apparatus according to claim 9, characterized in that said apparatus comprises a fixed diaphragm, a likewise fixed optical system receiving a parallel beam issuing from said diaphragm and a mobile screen which occults a central part of the beam passing through said optical system.

16. Apparatus according to one of claims 9 or 10, characterized in that said apparatus comprises a fixed diaphragm, a fixed optical system and a mobile screen pierced with a slot.

17. Apparatus according to claim 16, in which said mobile screen moves in a plane transverse to the beam, characterized in that said apparatus comprises means for adjusting the orientation of said slot in the plane of said mobile screen.

18. Apparatus according to claim 1 characterized in that said apparatus comprises an electronic computer means for controlling said source of light and said scanning means whereby the desired variation in thickness for said lamina to be eliminated may be produced by controlling the length of time each portion of said corneal surface is exposed to said source of light.

19. Apparatus according to claim 18, characterized in that said apparatus further comprises a Keratometer means for continuously following the evolution of the curvature of the part of the cornea being modified and of addressing measurements of said Keratometer to said computer.

20. Apparatus according to claim 18, characterized in that said apparatus further comprises an auxiliary laser generator means for aligning said beam with respect to said cornea.

21. A surgical apparatus useful in performing in situ opthamological operations to optimize the curvature of the anterior surface of an area of the cornea of an eye, having an optical axis comprising:
(a) a light source having a wavelength in the ultraviolet range, said light source being capable of effecting photochemical decomposition of corneal material;
(b) means for selecting out of the light produced by said light source, a portion of light which is essentially unidirectional in nature, whereby a beam of light having an outer portion and a center is formed;
(c) means for focusing said beam of light onto the anterior surface of a patient's cornea, whereby a light spot having an area a configuration is formed, the area of said light spot having a maximum area at least as large as the area of the cornea desired to be operated upon, whereby within the area of the corneal surface impinged by said light spot, ablation of a portion of the corneal material occurs by means of photochemical decomposition, said ablation being time-dependent, whereby, the longer a particular portion of the cornea surface is impinged by said light spot the greater the amount of corneal material ablated; and,
(d) means for changing the configuration of said light spot, whereby size or shape of said light spot may be varied or a portion of said light spot may be obscured such that, as a function of time, varying portions of the cornea surface may be made to receive varying amounts of total photoradiant energy, whereby a lenticular lamina of cornea material having a smooth anterior surface may be removed by ablation, thereby locally adjusting the radius of curvature of the cornea surface.

22. The surgical apparatus of claim 21 wherein said light source has a wavelength of about 200 nanometers.

23. The surgical apparatus of claim 21 wherein said means for producing a light beam which is essentially unidirectional in nature is a first diaphragm having a central aperture, whereby all light produced by said light source which is overly divergent with respect to said aperture is blocked.

24. The surgical apparatus of claim 21 wherein said means for focusing said beam of light onto the area of the patient's cornea desired to be ablated is a lens.

25. The surgical apparatus of claim 24 wherein said lens is biconvex.

26. The surgical apparatus of claim 21 wherein said light spot is round and is centered around the optical axis of the patient's eye, whereby said lenticular lamina of corneal material removed through ablation exhibits radial symmetry around said optical axis.

27. The surgical apparatus of claim 21 wherein said means for changing the configuration of said light spot is a second diaphragm having a central aperture, whereby said light beam may be focused such that the outer portion of said light beam is obscured by said second diaphragm, thereby producing a light spot smaller than the entire area of the cornea to be ablated.

28. The surgical apparatus of claim 21 wherein said means for changing the configuration of said light spot is a screen disposed within the path of said light beam and centered around said optical axis, whereby said screen creates a darkened area at the center of said light spot on the surface of the cornea such that a lenticular lamina of corneal material may be ablated which has a greater thickness at the periphery thereof than at the center thereof.

29. The surgical apparatus of claim 21 wherein said means for changing the configuration of said light spot is a screen having a substantially rectangular aperture disposed therein, said aperture disposed orthogonal to said optical axis whereby a substantially rectangular light spot may be formed on the surface of the patient's cornea.

30. The surgical apparatus of claim 29 further comprising means for displacing said substantially rectangular light spot away from said optical axis whereby corneal malformities which do not exhibit radial symmetry around said optical axis may be alleviated.

31. The surgical apparatus of claim 21 further including drive means for moving said means for focussing and stabilization means for stabilizing said means for focussing disposed parallel to said optical axis whereby said means for changing the configuration of said light spot may be moved in a controlled fashion along said optical axis.

32. The surgical apparatus of claim 21 further including drive means for moving said means for focussing and stabilization means for stabilizing said means for focussing disposed parallel to said optical axis whereby said means for focusing said light beam may be moved in a controlled fashion along said optical axis.

33. The surgical apparatus of claim 32 further comprising automated control means for controlling movement of said drive means.

* * * * *